(12) United States Patent
Hingston et al.

(10) Patent No.: US 9,498,296 B2
(45) Date of Patent: Nov. 22, 2016

(54) ATRAUMATIC STENTS INCLUDING RADIOPAQUE CONNECTORS AND METHODS

(71) Applicant: Boston Scientific Scimed, Inc., Maple Grove, MN (US)

(72) Inventors: John Allen Hingston, Framingham, MA (US); Gerald Fredrickson, Westford, MA (US); Peter Brady, Galway (IE); Shane McMahon, County Galway (IE); Gary O'Brien, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 106 days.

(21) Appl. No.: 14/455,373

(22) Filed: Aug. 8, 2014

(65) Prior Publication Data

US 2015/0045875 A1 Feb. 12, 2015

Related U.S. Application Data

(60) Provisional application No. 61/864,253, filed on Aug. 9, 2013.

(51) Int. Cl.
*A61F 2/915* (2013.01)
*A61B 19/00* (2006.01)
*A61F 2/90* (2013.01)

(52) U.S. Cl.
CPC .............. *A61B 19/54* (2013.01); *A61B 90/39* (2016.02); *A61F 2/90* (2013.01); *A61F 2/915* (2013.01); *A61F 2250/0032* (2013.01); *A61F 2250/0098* (2013.01); *Y10T 29/49906* (2015.01)

(58) Field of Classification Search
CPC ............... A61F 2/07; A61F 2/89; A61F 2/90
USPC .......................... 623/1.5–1.53, 1.34
See application file for complete search history.

(56) References Cited

U.S. PATENT DOCUMENTS

| | | | |
|---|---|---|---|
| 8,434,393 B2* | 5/2013 | Adams | A61F 2/90 87/11 |
| 2005/0283226 A1 | 12/2005 | Haverkost | |
| 2006/0129222 A1* | 6/2006 | Stinson | A61F 2/90 623/1.2 |

(Continued)

FOREIGN PATENT DOCUMENTS

| | | |
|---|---|---|
| DE | 102011015995 A1 | 10/2012 |
| WO | 2006053270 A2 | 5/2006 |

OTHER PUBLICATIONS

PCT International Search Report, PCT International Application No. PCT/US2014/050378 (Filing Date: Aug. 8, 2014); mailed Oct. 15, 2014; 4 pgs.

(Continued)

*Primary Examiner* — Suzette J Gherbi
(74) *Attorney, Agent, or Firm* — Seager, Tufte & Wickhem, LLP

(57) ABSTRACT

The invention is directed to a stent including at least one member having a first portion and a second portion and at least one radiopaque connector joining the first portion to the second portion. In one or more embodiments, at least one radiopaque connector may form a first radiopaque pattern distinguishable from a second radiopaque pattern formed by at least one radiopaque marker. Methods for manufacturing a stent including at least two member portions connected by at least one radiopaque connector are also provided.

20 Claims, 1 Drawing Sheet

(56) References Cited

U.S. PATENT DOCUMENTS

| | | | | |
|---|---|---|---|---|
| 2009/0210048 A1* | 8/2009 | Amplatz | ............... | A61F 2/07 623/1.13 |
| 2009/0259125 A1* | 10/2009 | Stinson | ............ | A61B 17/12022 600/431 |
| 2010/0063578 A1* | 3/2010 | Ren | ............... | A61F 2/07 623/1.15 |
| 2010/0094400 A1* | 4/2010 | Bolduc | ............ | A61B 17/00234 623/1.11 |
| 2012/0071964 A1 | 3/2012 | Cattaneo et al. | | |
| 2012/0259404 A1* | 10/2012 | Tieu | ............... | A61F 2/852 623/1.15 |
| 2013/0197627 A1* | 8/2013 | Jensen | ............... | A61F 2/07 623/1.35 |
| 2013/0245745 A1* | 9/2013 | Vong | ............... | A61F 2/885 623/1.12 |
| 2014/0180397 A1* | 6/2014 | Gerberding | ............ | A61F 2/852 623/1.16 |
| 2014/0288637 A1* | 9/2014 | Clerc | ............... | A61F 2/90 623/1.22 |
| 2015/0045874 A1* | 2/2015 | McMahon | ............... | A61F 2/88 623/1.22 |
| 2015/0126920 A1* | 5/2015 | Dickinson | ............ | A61M 27/002 604/8 |
| 2015/0342765 A1* | 12/2015 | Weiner | ............... | A61F 2/95 623/9 |

OTHER PUBLICATIONS

PCT Written Opinion of the International Searching Authority, PCT International Application No. PCT/US2014/050378 (Filing Date: Aug. 8, 2014); mailed Oct. 15, 2014; 6 pgs.

* cited by examiner

ATRAUMATIC STENTS INCLUDING RADIOPAQUE CONNECTORS AND METHODS

CROSS REFERENCE TO RELATED APPLICATIONS

This application claims the benefit of and priority to U.S. Provisional Patent Application No. 61/864,253, filed Aug. 9, 2013.

FIELD

The present disclosure relates to stents including one or more radiopaque connectors and methods of manufacturing the same.

BACKGROUND

A stent is a medical device introduced into a body lumen and is well known in the art. A stent may be delivered in an unexpanded state to a desired location in a bodily lumen and then expanded by an internal radial force. Stents, grafts, stent-grafts, vena cava filters, expandable frameworks, and similar implantable medical devices, collectively referred to hereinafter as stents, have included radially expandable endoprostheses, which have been used as intravascular implants capable of being implanted transluminally.

When implanting a stent in a patient's body lumen, an operator (e.g., a physician, etc.) may wish to verify that stent placement and/or orientation are appropriate to the particular stent application and implantation site. Some stents have been known to include a radiopaque marker so that the marker may be visible via, for example, fluoroscopy. Viewing a radiopaque marker via fluoroscopy may allow monitoring of the stent position during and following delivery and deployment.

There are drawbacks associated with radiopaque markers. In terms of manufacturing, some radiopaque markers have been difficult to secure to the stent. In terms of stent design, in which the trend is toward thinner stent walls, some radiopaque markers contribute an undesirable additional thickness.

Some stents are made from wires or filaments having ends that are loose. Loose ends of stent members (e.g., longitudinal members such as wires, filaments, etc.) have been known to cause trauma to the wall of the body lumen during and after delivery and deployment, resulting in increased patient discomfort and increased recovery times.

Some stents have been designed to reduce the traumatic effect of the wire/structure ends (e.g., loose ends) at the most distal and/or proximal end of the stent by enclosing the wire/structure ends with, for example, a drop of molten material. However, some of these stent designs do not result in an atraumatic end. An atraumatic end of a stent refers to a wire/structure end of a stent (e.g., a terminal end) which is smooth, free of sharp wire ends or other sharp projections or deformities which may cause trauma when implanted into a body lumen.

There is an ongoing need for improved visibility of stents during and after delivery and deployment and reduced stent profiles. There is also an ongoing need for improved methods of manufacturing stents that, for example, reduce the number of manufacturing steps, reduce the cost of manufacturing, and/or reduce the number of and/or cost of raw materials.

Without limiting the scope of the present disclosure, a brief summary of some of the claimed embodiments is provided below. Additional details of the summarized embodiments and/or additional embodiments can be found in the detailed description.

All US patents and applications and all other published documents mentioned anywhere in this application are incorporated herein by reference in their entirety.

SUMMARY

One or more aspects of the present disclosure relates to a stent that includes a tubular structure. The tubular structure has a first section and a second section. The tubular structure defines a lumen that extends through the first section and the second section. The tubular structure includes at least one member having a first portion and a second portion. The tubular structure also includes at least one radiopaque connector joining the first portion to the second portion.

One or more aspects of the present disclosure relates to a stent including a tubular structure. The tubular structure includes a first section that includes at least one radiopaque connector that joins a first portion of at least one member to a second portion of the at least one member. In one or more embodiments, the at least one radiopaque connector forms a first radiopaque pattern. The tubular structure includes a second section that includes at least one radiopaque marker forming a second radiopaque pattern that is different from the first radiopaque pattern when viewed under fluoroscopy. In one or more embodiments, the tubular structure defines a lumen extending through the first section and the second section. In some embodiments, the first section of the tubular structure is atraumatic.

One or more aspects of the present disclosure relates to a method of manufacturing a stent. The method includes forming a tubular structure having a first section and a second section, wherein the tubular structure defines a lumen extending through the first section to the second section. In one or more embodiments, the tubular structure includes at least one member (e.g., a longitudinal member). In one or more embodiments, each of the at least one member includes a first portion and a second portion. The method further includes joining at least one first portion to a second portion. In one or more embodiments, the joining includes contacting a radiopaque joining composition to the first portion and the second portion, wherein the radiopaque joining composition comprises a polymer and a radiopaque material. In one or more embodiments, joining includes allowing the radiopaque joining composition to harden, thereby forming a radiopaque connector.

BRIEF DESCRIPTION OF THE FIGURES

A detailed description is hereafter provided with specific reference being made to the drawings.

DETAILED DESCRIPTION

Figure 2:
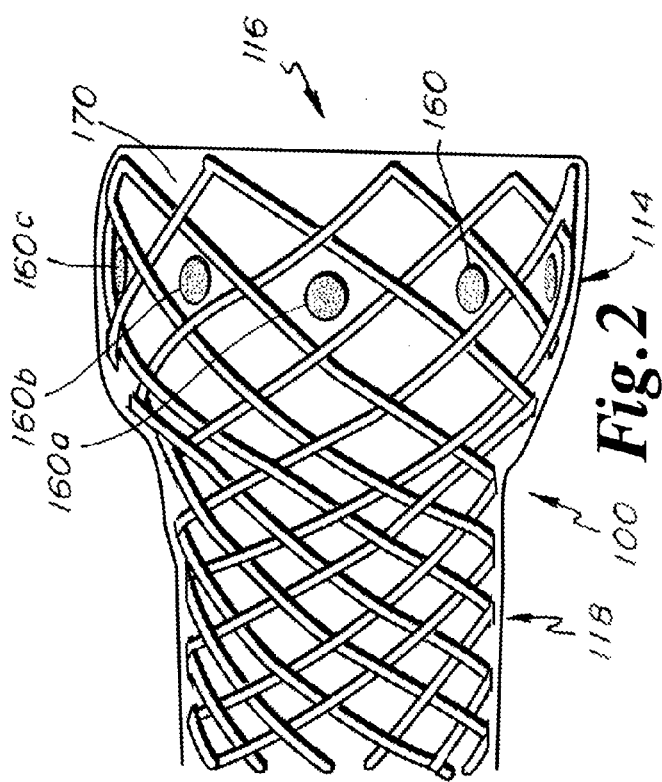
FIG. 2 shows a photograph of at least one embodiments of a second section (and an optional medial section) of a stent in accordance with one or more embodiments of the present disclosure.

While the subject matter of the present disclosure can be embodied in many different forms, specific embodiments are described in detail herein. This description is an exemplification of the principles of the present disclosure and is not intended to limit the present disclosure to the particular embodiments illustrated.

For the purposes of this disclosure, like reference numerals in the figures shall refer to like features unless otherwise indicated.

Various aspects of the present disclosure are depicted in the figures. Elements depicted in one figure can be combined with and/or substituted for elements depicted in another figure as desired.

The terms proximal and distal, described in relation to various devices, apparatuses, and components as discussed in the subsequent text of the present disclosure, are referred with a point of reference. The point of reference, as used in this description, is a perspective of an operator. The operator can be a surgeon, a physician, a nurse, a doctor, a technician, and the like, who can perform the procedure of delivery and placement of the disclosed system/device into the patient's body as described in the present disclosure. The term proximal refers to an area or portion that is closer or closest to the operator during a placement procedure. The term distal refers to an area or portion that is further or farthest from the operator.

Figure 1:
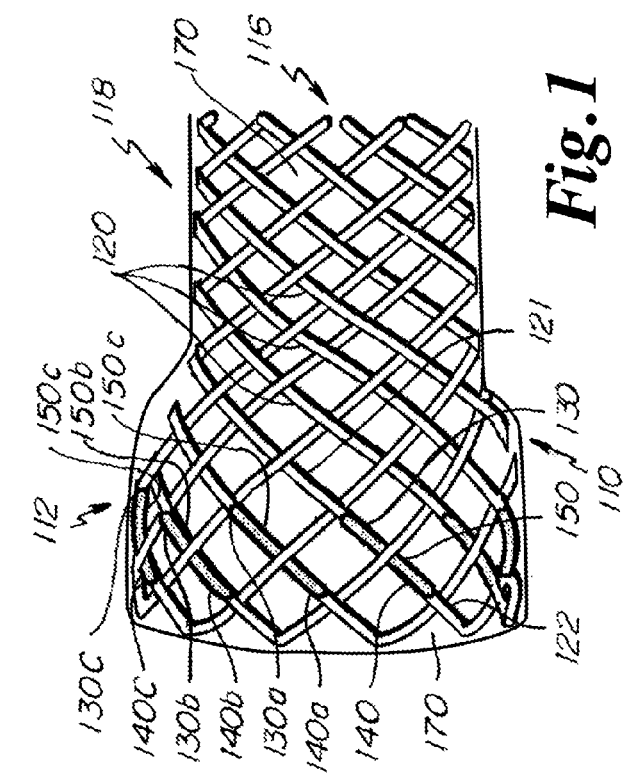
FIG. 1 shows a photograph of at least one embodiment of a first section (and an optional medial section) of a stent in accordance with one or more embodiments of the present disclosure.

Referring now to FIG. 1, a portion of a stent 100 is shown. Stent 100 includes a tubular structure 110. The tubular structure has a first section 112 and a second section 114 (shown in FIG. 2). The tubular structure also defines a lumen 116 extending through the first section 112 and the second section.

In one or more embodiments, the tubular structure 110 includes at least one member 120 (e.g., a longitudinal member, etc.) having a first portion 130 and a second portion 140. In the present disclosure, member 120 may include a longitudinal member, such as a wire or a filament (e.g., a monofilament, etc.). Each member 120 may include a plurality of longitudinal members (e.g., a wire, a filament, etc.), wherein the plurality of longitudinal members may be braided or otherwise secured to form a single member 120. In one or more embodiments, the at least one member includes polyethylene terephthalate (PET) filament (e.g., monofilament).

In one or more embodiments, the tubular structure 110 includes at least one radiopaque connector 150 joining the first portion 130 to the second portion 140. In one or more embodiments, the at least one radiopaque connector 150 provides a structural connection between the first portion 130 and the second portion 140 and forms a first pattern visible when viewed by, for example, fluoroscopy. In the present disclosure, "radiopaque connector" refers to a radiopaque article that serves as a marker (e.g., a radiopaque marker) and also connects (e.g., joins, secures, etc.) a first portion of at least one member to a second portion of the at least one member (e.g., the same member as or a different member than the member of the first portion), "radiopaque marker" refers to a radiopaque article that serves as a marker and does not connect a first portion of at least one member to a second portion of the at least one member, and "radiopaque feature" refers to a radiopaque connector or a radiopaque marker.

As discussed herein, stents having a lack of loose ends capable of contacting a body lumen wall may be useful in order to, for example, reduce patient discomfort and/or reduce recovery time. In one or more embodiments, the members 120 and radiopaque connectors of the tubular structure 110 are structured and arranged such that at least the first section 112 of the tubular structure 110 is atraumatic. In an atraumatic first section, all of the first portions 130 are paired with and joined to (e.g., secured to) a second portion 140, resulting in no loose member ends. In one or more embodiments, an atraumatic first section may be an atraumatic end of the tubular structure. In one or more embodiments, the second section 114 is atraumatic. In at least one embodiment, stent 100 is atraumatic (e.g., at both ends).

In one or more embodiments, the at least one radiopaque connector 150 connects (e.g., joins, secures, bonds, adheres, welds, etc.) a first portion 130 to a second portion 140 via a lap joint, side-by-side joint, or a butt joint. In one or more embodiments, a first portion 130 may be secured to a second portion 140 without direct contact between the first portion 130 and the second portion 140 (e.g., the radiopaque connector 150 may be disposed between the first portion 130 and the second portion 140).

In one or more embodiments, the at least one member 120 includes a wire (e.g., a metallic wire) and/or a filament (e.g., a polymer filament, a polymer monofilament, etc.). The at least one member 120 may include or be formed from any of a wide variety of materials known in the art. For example, the at least one member 120 may include or may be formed from one or more polymers (e.g., a polymer mixture, a polymer blend, a copolymer, etc.) and/or a metal or a plurality of metals (e.g., an alloy, etc.). In one or more embodiments, the at least one member 120 is a polymeric filament formed from one or more polymers.

The at least one member 120 may include any suitable number of members (e.g., a first member, a second member, a third member, etc.). In one or more embodiments, a tubular structure 110 may include at least 2 members, at least 6 members, at least 12 members, at least 18 members, at least 24 members, at least 36 members, etc. In one or more embodiments, the tubular structure includes a braid (e.g., a braided configuration) formed from the at least one member 120.

In one or more embodiments, the at least one member 120 includes a first member 121 and a second member 122, wherein each of the first member 121 and second member 122 includes a first portion 130 and a second portion 140. For example, as shown in FIG. 1, first member 121 includes a first portion 130 and second member 122 includes a second portion 140 contacting (e.g., extending within, etc.) a radiopaque connector 150. In one or more embodiments, the second portion of first member 121 and the first portion of second member 122 are not shown in FIG. 1. In one or more embodiments in which both first member 121 and second member 122 extend toward the second section 114, bend, and extend back toward the first section, the second portion of first member 121 and the first portion of second member 122 may contact (e.g., extend within, etc.) a different radiopaque connector 150 (e.g., 150a, 150b, 150c, etc.) of the first section 112.

In one or more embodiments in which the at least one member 120 includes a plurality of members (e.g., a first member 121 and a second member 122), the at least one radiopaque connector 150 may include a plurality of radiopaque connectors 150 (e.g., a first radiopaque connector and a second radiopaque connector), wherein each of the plurality of radiopaque connectors 150 joins a first portion 130 of one of the plurality of members 120 (e.g., of the first or second member) to a second portion 140 of itself or of another of the plurality of members (e.g., of the first or second member).

In one or more embodiments, the at least one member 120 may be a single member (e.g., a single wire, a single filament, etc.) having a first portion 130 and a second portion 140.

In one or more embodiments, the first portion 130 includes a first end portion of the at least one member 120. In one or more embodiments, a first end portion includes a first terminal endpoint of a member 120. In one or more embodiments, the second portion 140 includes a second end portion of the at least one member 120, wherein the second end portion includes a second terminal endpoint of a member 120. For example, in FIG. 1, a first terminal endpoint of a first portion 130 of member 121 and a second terminal endpoint of a second portion 140 of member 122 are obscured by the radiopaque connector 150.

Figure 3:
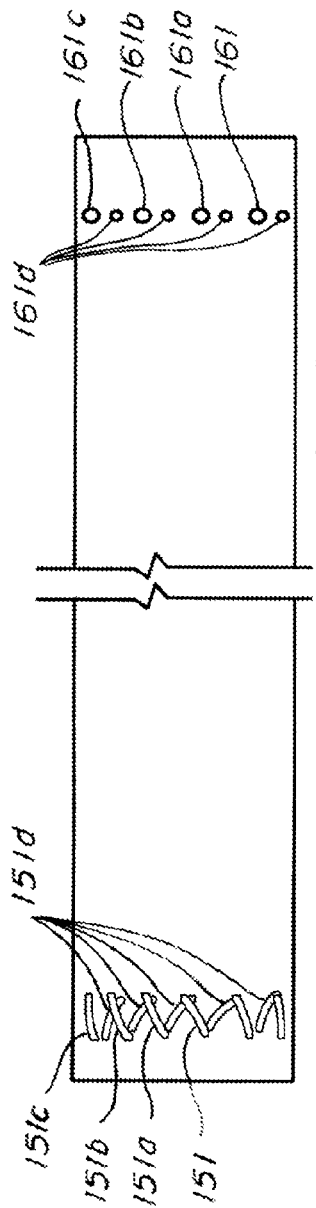
FIG. 3 shows a schematic showing two patterns of shapes of radiopaque features of FIGS. 1 and 2 as may be observed under fluoroscopy.

In another aspect of the present disclosure, a first section 112 may include at least one radiopaque connector that joins a first portion 130 of at least one member 120 to a second portion 140 of the at least one member 120, the at least one radiopaque connector 150 forming a first radiopaque pattern (e.g., visible on the stent as a plurality of line segments as in FIG. 1, visible in a fluoroscopic display as a plurality of line segments as schematically depicted in FIG. 3, etc.). In one or more embodiments, the first radiopaque pattern includes a plurality of longitudinal shapes, each corresponding with a radiopaque connector. In at least one embodiment, as shown in FIG. 1, each of the radiopaque connectors 150 may be oriented generally parallel to the first portion 130 and/or the second portion 140 of the at least one member 120. Of course, other orientations are possible and may be envisioned by one of skill in the art.

As discussed herein, when implanting a stent, it may be useful to verify accuracy of stent location and/or stent orientation. Stent location and orientation may be observed and/or verified by using, for example, fluoroscopy, wherein the radiopaque features of a stent may be displayed and/or viewed. Thus, the arrangement of radiopaque features may allow improved monitoring of stent placement and/or orientation. In one or more embodiments, providing a different radiopaque pattern in one section of the stent relative to a second radiopaque pattern in another section of the stent may allow verification of, for example, location and/or orientation of the stent.

Patterns of radiopaque features may differ due to any of a wide variety of possible modifications. For example, a first pattern may differ from a second pattern in the number of radiopaque features (e.g., number of radiopaque connectors relative to number of radiopaque markers), the shape of individual radiopaque features (e.g., longitudinal in FIG. 1 relative to circular in FIG. 2), the arrangement of individual radiopaque features within a pattern, the radiopaque material (e.g., which may affect the radiopacity of one or more of the radiopaque features of a particular pattern), the size of one or more of the individual radiopaque features of a particular pattern, etc. Many other modifications will be apparent to one of skill in the art to distinguish a first pattern from a second pattern.

In one or more embodiments, a stent 100 may include at least one radiopaque marker 160 at or near the second section 114 of the tubular structure 110. In one or more embodiments, the at least one radiopaque marker 160 at or near the second section 114 of the tubular structure 110 has a size, radiopacity, shape, quantity, and/or pattern that is distinguishable from the at least one radiopaque connector 150 when viewed by fluoroscopy. In one or more embodiments, the at least one radiopaque marker has a circular shape (e.g., formed by a drop), a four-sided shape (e.g., taking the shape of the stent braid diamond). In other words, the at least one radiopaque connector 150 may form a first pattern when viewed under fluoroscopy and the at least one radiopaque marker 160 may form a second pattern when viewed under fluoroscopy. In one or more embodiments, first pattern is different and distinguishable from the second pattern when the stent is viewed under fluoroscopy. The at least one radiopaque marker 160 may include any suitable number of radiopaque markers 160 (e.g., at least two, at least three, at least four, at least 8, at least 12, at least 16, at least 24, etc.).

In one or more embodiments, the size, radiopacity, and shape are uniform among all of the at least one radiopaque connector 150. In one or more embodiments, one or more radiopaque connectors may have a different size, radiopacity, and/or shape than one or more other radiopaque connectors. Similarly, the radiopaque markers 160 may have uniformity or nonuniformity of size, radiopacity, and/or shape.

In one or more embodiments, a second section 114 may include at least one radiopaque marker 160 forming a second radiopaque pattern that is different from the first radiopaque pattern (e.g., of radiopaque connectors 150) when viewed under fluoroscopy. In the one or more embodiments of FIG. 2, the at least one radiopaque marker 160 includes a plurality of radiopaque markers 160, wherein each is disposed an equidistant length from an end (e.g., a second end) of the stent 100. In one or more embodiments, not all of the radiopaque markers 160 are disposed at a uniform distance from a stent end.

With reference to FIG. 1, each of the radiopaque connectors 150 would appear on a fluoroscopy display as a line having a length of approximately two cells and a thickness of approximately the same width as the members 120. Depending on the orientation of the stent 100, the plurality of radiopaque connectors 150 may appear on a fluoroscopy image as a plurality of lines that may be overlapping, indicating a side view (as shown in FIG. 1) or may appear as a plurality of lines wherein some of the lines are offset, indicating a different orientation.

For example, FIG. 3 shows a schematic of an image as might be obtained from fluoroscopy, showing the radiopaque features of stent 100 of FIGS. 1 and 2. FIG. 3 shows a first pattern of radiopaque connector shapes (e.g., 151, 151*a*, 151*b*, 151*c*, etc.), each shape corresponding with a radiopaque connector (e.g., 150, 150*a*, 150*b*, 150*c*) of FIG. 1. Some radiopaque connector shapes 151*d* shown in FIG. 3 correspond with radiopaque connectors 150 that cannot be seen in FIG. 1 because they are obscured by stent 100.

FIG. 3 also shows a second pattern of radiopaque marker shapes (e.g., 161, 161*a*, 161*b*, 161*c*, etc.), each shape corresponding with a radiopaque marker (e.g., 160, 160*a*, 160*b*, 160*c*) of FIG. 2. Some radiopaque marker shapes 161*d* shown in FIG. 3 correspond with radiopaque markers 160 that cannot be seen in FIG. 2 because they are obscured by stent 100. In one or more embodiments, the sizes of radiopaque markers 160 may vary, resulting in differently sized radiopaque marker shapes 161 in FIG. 3 One of ordinary skill in the art will appreciate that each of the schematically-represented shapes outlined in FIG. 3 (e.g., corresponding to each of the radiopaque connectors and radiopaque markers) would generally appear as a filled-in shape having a shade or color that contrasts with the background around the shapes.

In FIG. 3, radiopaque marker shapes 161 forming a second pattern may be viewed in relation to a first pattern of radiopaque connector shapes 151. In this way, a spatial relationship between the first section 112 and the second section 114 may be observed, as well as an indication of the orientation or skew of the stent 100.

In FIG. 3, the radiopaque connector shapes 151 are arranged such that the proximal ends are generally aligned, indicating that the side of stent 100 is being viewed. Similarly, the alignment of radiopaque marker shapes 161 in a line also indicate that the perspective of the fluoroscopic device is from a side view of stent 100. If, for example, the radiopaque marker shapes 161 were arranged in an ellipse, the pattern would indicate that the stent is oriented with some amount of skew relative to the orientation shown in FIG. 3.

In the present disclosure, radiopaque features (e.g., radiopaque connectors 150 and radiopaque markers 160) may include and/or be formed from any of a wide variety of radiopaque materials. As disclosed herein, radiopaque connectors 150 may include the same or different radiopaque materials as the radiopaque markers 160. A radiopaque material may include, but is not limited to, tungsten. A radiopaque feature may, in some embodiments, include two or more radiopaque materials.

In one or more embodiments, the radiopaque connector 150 includes a polymer (e.g., a thermoplastic polymer). In other words, a radiopaque connector 150 of the present disclosure is a combination of radiopaque material and joining material. In one or more embodiments, joining material may include a commercially available material such as MED-4213, MED-6342, and MED 9345 (NuSil Technology LLC, Carpinteria, Calif.), or a silicone such as MED 4820 (NuSil Technology LLC, Carpinteria, Calif.). In one or more embodiments, a radiopaque connector 150 may include an adhesive polymer, a hot melt polymer (e.g., polyethylene terephthalate (PET)), a molten plastic, and/or a silicone polymer (e.g., a medical silicone, an addition-cured silicone providing adequate adhesion). In one or more embodiments, a hot melt polymer may include, but is not limited to, polyolefins such as polyethylene and polypropylene, polybutylene, and copolymers and terpolymers of ethylene such as ethylene vinyl acetate, ethylene-methacrylic acid and ethylene-acrylic acid copolymers where some of the acid groups have been neutralized with cations, for example zinc or sodium ions (commonly known as ionomers), copolymers and terpolymers of propylene and butylene, metallocene catalyzed polyethylenes, chloropolymers such as polyvinylchloride, fluoropolymers such as polytetrafluoroethylenes and fluorinated ethylene propylene, polyvinyl acetate, polyesters such as poly(ethylene terephthalate) and poly(butylene terephthalate), naphthalene dicarboxylate derivatives such as polyethylene naphthalate, polybutylene naphthalate, polytrimethylene naphthalate and trimethylenediol naphthalate, polyurethane, polyurea, polyamides such as nylon 6 and nylon 6,6 polyimides, polycarbonates, polyaldehydes, polyether ether ketone, natural rubbers, polyester copolymers, polyethers such as fully or partially halogenated polyethers, vinyl aromatic homopolymers such as polystyrene, vinyl aromatic elastomers such as styrenic block copolymers, alkyl acrylates and methacrylate polymers and copolymers, polyacetals, polyester-ethers, polyamide ethers, elastomers such as elastomeric polyurethanes and polyurethane copolymers and poly(ether-block-amide) block copolymers, methylmethacrylate N-vinylpyrrolidone copolymers, and blends, mixtures and copolymers of any of the foregoing. In one or more embodiments, the joining material and the first portion 130 or second portion 140 are formed of the same material (e.g., PET joining material and PET monofilaments). In at least one embodiment, a radiopaque connector 150 may include a thermoplastic polymer (e.g., polyethylene terephthalate) combined with tungsten.

In the present disclosure, a stent 100 may include other sections besides a first section 112 and a second section 114. For example, a stent 100 may include a medial section 118 disposed between the first section 112 and the second section 114. With reference to FIG. 1, the medial section 118 may extend from a first section 112. In one or more embodiments in which a medial section 118 has a diameter that is different (e.g., smaller) than the first section 112 diameter, a diameter transition portion (e.g., a cone portion, etc.) may connect the first section 112 to the medial section 118.

Similarly, with reference to FIG. 2, a medial section 118 may extend from a second section 114, may have a diameter that is different (e.g., smaller) than the second section 114 diameter, and may be connected to the second section 114 via a diameter transition portion (e.g., a cone portion, a frustoconical portion, etc.).

In one or more embodiments, a medial section 118 may have the same diameter as one or both of the first section 112 and second section 114.

In one or more embodiments, a medial section 118 may include a plurality of diameters along the longitudinal length of the medial section 118. In one or more embodiments, a medial section 118 may include one or more radiopaque features that may be arranged in one or more medial section patterns (e.g., regular pattern and/or irregular pattern) that may be the same as or different than one or both of the first section 112 and the second section 114.

Stents of the present disclosure may have any size without limitation. In one or more embodiments, the design parameters of a stent (e.g., the length, diameter, thickness, etc.) may be selected depending on the application and implantation site. Stents of the present disclosure may be suitable for any of a wide variety of body lumens (e.g., esophageal, biliary, colonic, duodenal, blood vessels, etc.).

Another aspect of the present disclosure includes a method of manufacturing a stent 100. The method includes forming a tubular structure 110 having a first end section 112 and a second section 114 and defining a lumen 116 extending through the first section 112 to the second section 114. As described herein, the tubular structure 110 includes at least one member 120, each of the at least one member 120 including a first portion 130 and a second portion 140.

Forming the tubular structure may be performed using any of a wide variety of forming techniques. For example, forming the tubular structure 110 may include braiding the at least one member 120. Braiding at least one member 120 may be performed using, for example, a mandrel (e.g., a braiding mandrel). In one or more embodiments, the tubular structure may be formed from a single member 120 (e.g., a wire) or may be formed from a plurality (e.g., 18, etc.) of members. In one or more embodiments, the tubular structure may be weaved formed (e.g., woven, etc.) or knitted formed (e.g., knitted, etc.). In one or more embodiments, the tubular structure may be formed by laser cutting a tube in a predefined pattern to form a tubular structure. In one or more embodiments, the tubular structure may be formed by joining together pre-made rings together.

The method also includes joining at least one first portion 130 to a second portion 140. In the one or more embodiments in which forming includes braiding the at least one member 120 to form a tubular structure 110, the joining of the at least one first portion 130 to a second portion 140 occurs after the braiding. In one or more embodiments, the joining may be performed before coating the stent (e.g., on a coating mandrel). Joining may include axially aligning a first portion 130 with a second portion 140. Aligning a first portion 130 with a second portion 140 may include arranging the first portion 130 and second portion 140 in an end-to-end (e.g., coaxial, etc.) arrangement, in a side-by-side arrangement (e.g., wherein the first portion and second portion are generally parallel), or in another arrangement.

In one or more embodiments, the joining includes contacting a radiopaque joining composition to the first portion 130 and the second portion 140 (e.g., for subsequent attachment). Contacting a radiopaque joining composition to the first portion 130 and the second portion 140 may be performed using any of a wide variety of techniques including, but not limited to, dipping, spraying, applying, brushing, and dripping. In one or more embodiments, a radiopaque joining composition includes a solid thermoplastic that may be melted and contacted with the first portion 130 and the second portion 140. In one or more embodiments, the melting of the thermoplastic may be accomplished using welding, heating, laser joining, and/or ultrasonic joining techniques.

In the present disclosure, a radiopaque joining composition may include a radiopaque material and one or more hardenable components. In one or more embodiments, the radiopaque material may be mixed with and/or disposed within the one or more hardenable components. A hardenable component may include, but is not limited to a polymer, a pre-polymer, a polymer precursor, a monomer, an oligomer. A hardenable component may be combined with an optional delivery component such as a solvent or other carrier liquid to aid with dispensing the radiopaque joining composition.

In the one or more methods of the present disclosure, joining includes allowing the radiopaque joining composition to harden. Allowing a radiopaque joining composition to harden may include curing the composition, exposing the composition to UV light, heating the composition, cooling the composition, applying pressure to the composition, contacting two reactants and allowing a chemical reaction to occur, polymerizing one or more components (e.g., monomers, oligomers, polymer precursors, etc.), crosslinking one or more components (e.g., polymers, etc.), etc. The hardening of the radiopaque joining composition thereby forms a radiopaque connector that, in at least one embodiment, provides structural support to the joint between the first portion 130 and the second portion 140 and provides a radiopaque aspect (e.g., a marker) that may be viewed by, for example, fluoroscopy.

In one or more embodiments, the joining of the at least one first portion 130 to a second portion 140 occurs at or near one or more of the first section 112 of the tubular structure 110, the second section 114 of the tubular structure 110, the medial section 118 of the tubular structure 110, and/or in a diameter transition portion disposed between a larger diameter section of stent 100 and a smaller diameter section of stent 100. For example, in FIG. 1, the joining occurs at the location of radiopaque connector 150, which extends not more than three cells from the first end of the stent 100. In one or more embodiments, the radiopaque connector 150 extends greater than three cells (e.g., greater than 5 cells, greater than 10 cells, etc.) from the first end of the stent 100. In FIG. 1, radiopaque connector 150 extends no closer than 1 cell from the first end of stent 100. In some embodiments, the radiopaque connector 150 extends at least to the first end of stent 100. In some embodiments, radiopaque connector extends no closer than 2 cells (e.g., no closer than 5 cells, no closer than 10 cells, etc.) from the first end of stent 100.

In one or more embodiments, stents of the present disclosure include a joining composition that is radiopaque, which may allow for a reduced stent profile. In some embodiments, stents of the present disclosure may allow for improved monitoring by fluoroscopy due to the distinctive patterns of radiopaque features. In some embodiments, methods of the present disclosure may reduce the number of manufacturing steps and may reduce the need for expensive manufacturing equipment since joining loose ends (e.g., first portion 130 and second portion 140) and applying a radiopaque feature are simultaneously performed. In one or more embodiments, the use of one or more radiopaque connectors may be used to remove a welding process step and thus reduce product manufacturing costs. The use of one or more radiopaque connectors may also be used reduce product cost of manufacturing materials. For example, a radiopaque core (e.g., a platinum core) from nitinol wire, which has been used in metal stents, may be optional when utilizing the one or more radiopaque connectors described herein. Thus, produce cost of one or more manufacturing materials (e.g., platinum) may be reduced or eliminated in some embodiments relative to stents that include a greater quantity of such manufacturing materials.

In one or more embodiments, a radiopaque connector 150 has a width that is 300% or less (e.g., 250% or less, 200% or less, 150% or less, 110% or less) of the width of at least one of the portions (e.g., first portion 130 and second portion 140) secured by the radiopaque connector 150.

In one or more embodiments of the present disclosure, a stent 100 may include a coating 170. In one or more embodiments, at least a portion of the coating 170 is disposed on the inside surface of the tubular structure 110 to form a wall defining lumen 116 and/or on the outside surface of the tubular structure to form an outer wall of stent 100. The coating 170 may extend in longitudinal and circumferential directions along at least a portion of the first section 112, the second section 114, and/or a medial section 118. It may be useful for the coating to extend from a first end of tubular structure 110 to a second end of tubular structure 110 and around the entire circumference of tubular structure 110.

Many stent coating materials are known in the art. Any of a wide variety of stent coating compositions known to one of skill in the art may be useful to form a coating 170. In one or more embodiments, a coating 170 may include silicone.

In at least one embodiment of the present disclosure, a method may include coating at least a portion of (e.g., the entirety of) the tubular structure 110 with a coating composition (e.g., that may harden to form a coating 170). In one or more embodiments, the coating occurs after the joining (e.g., after the at least one radiopaque connector 150 joins the first portion 130 to the second portion 140). Thus, in some embodiments, the coating 170 extends over the at least one radiopaque connector 150 and provides additional structural support to each joint in which a radiopaque connector joins a first portion 130 and a second portion 140.

Another aspect of the present disclosure relates to a stent 100 formed by any of the methods described herein.

A description of some exemplary embodiments of the present disclosure can be contained in the following numbered statements:

Statement 1. A stent comprising:

a tubular structure having a first section and a second section, wherein the tubular structure defines a lumen extending through the first section and the second section, and wherein the tubular structure comprises:
  at least one member having a first portion and a second portion;
  at least one radiopaque connector joining the first portion to the second portion.

Statement 2. The stent of statement 1 wherein the second portion is a second end portion of the at least one member.

Statement 3. The stent of statement 1 or statement 2 wherein the at least one member comprises a first member and a second member, wherein each of the first member and second member comprises a first portion and a second portion, and wherein the at least one radiopaque connector comprises a first and second radiopaque connector, wherein each of the first and second radiopaque connectors joins a first portion to a second portion.

Statement 4. The stent of statement 1 or statement 2 wherein the at least one member comprises a plurality of members, each member having a first portion and a second portion, and wherein the at least one radiopaque connector comprises a plurality of radiopaque connectors, each of the plurality of radiopaque connectors joining the first portion of one of the plurality of members to the second portion of another of the plurality of members.

Statement 5. The stent of any one of statements 1-4 wherein the first section of the tubular structure is atraumatic.

Statement 6. The stent of any one of statements 1-5 wherein the at least one member comprises a wire or a filament.

Statement 7. The stent of any one of statements 1-6 wherein the at least one member comprises a polymer.

Statement 8. The stent of any one of statements 1-7 wherein the at least one member comprises a metal.

Statement 9. The stent of any one of statements 1-8 wherein the radiopaque connector comprises a radiopaque material.

Statement 10. The stent of statement 9 wherein the radiopaque material comprises a polymer.

Statement 11. The stent of statement 10 wherein the polymer is selected from the group consisting of an adhesive polymer, a hot melt polymer, a silicone, and polyethylene terephthalate.

Statement 12. The stent of any one of statements 1-10 further comprising at least one radiopaque marker at or near the second section of the tubular structure.

Statement 13. The stent of statement 12 wherein the at least one radiopaque marker at or near the second section of the tubular structure has a shape or pattern that is distinguishable from the at least one radiopaque connector when viewed by fluoroscopy.

Statement 14. The stent of any one of statements 1-13 wherein the radiopaque connector comprises a lap joint, side-by-side joint, or a butt joint.

Statement 15. A stent comprising:
  a tubular structure comprising:
    a first section comprising at least one radiopaque connector that joins a first portion of at least one member to a second portion of the at least one member, the at least one radiopaque connector forming a first radiopaque pattern, and
    a second section comprising at least one radiopaque marker forming a second radiopaque pattern that is different from the first radiopaque pattern when viewed under fluoroscopy, and
    wherein the tubular structure defines a lumen extending through the first section and the second section, and wherein the first section of the tubular structure is atraumatic.

Statement 16. The stent of statement 15, the tubular structure further comprising a medial section having a diameter smaller than at least one of the first section and the second section, the medial section extending between the first section and the second section.

Statement 17. The stent of statement 15 or statement 16 wherein tubular structure comprises a braid formed from the at least one member.

Statement 18. The stent of any one of statements 15-17 wherein the first radiopaque pattern comprises a plurality of longitudinal radiopaque connectors.

Statement 19. The stent of any one of statement 15-18 wherein each of the radiopaque connectors is oriented generally parallel to the first portion or the second portion of the at least one member.

Statement 20. A method of manufacturing a stent comprising:
  forming a tubular structure having a first section and a second section,
    wherein the tubular structure defines a lumen extending through the first section and the second section,
    wherein the tubular structure comprises at least one member, each of the at least one member comprising a first portion and a second portion;
  joining at least one first portion to a second portion, wherein the joining comprises:
  contacting a radiopaque joining composition to the first portion and the second portion, wherein the radiopaque joining composition comprises a polymer and a radiopaque material;
  allowing the radiopaque joining composition to harden, thereby forming a radiopaque connector.

Statement 21. The method of statement 20 wherein joining at least one first portion to a second portion occurs at or near the first section of the tubular structure.

Statement 22. The method of statement 20 or statement 21 wherein forming a tubular structure comprises: braiding at least one member on a braiding mandrel.

Statement 23. The method of statement 22 wherein the joining occurs after the braiding.

Statement 24. The method of any one of statements 20-23 further comprising: coating the tubular structure with a coating composition.

Statement 25. The method of statement 24, wherein the coating occurs after the joining.

Statement 26. The stent formed by the method of any one of statements 20-25.

The above disclosure is intended to be illustrative and not exhaustive. This description will suggest many variations and alternatives to a person of ordinary skill in this art. The various elements shown in the individual figures and described above can be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the detailed description. Those skilled in the art can recognize other equivalents to the specific embodiment described herein which equivalents are intended to be encompassed by the claims attached hereto.

The invention claimed is:

1. A stent comprising:
    a tubular structure having a first section and a second section, wherein the tubular structure defines a lumen extending through the first section and the second section, and wherein the tubular structure comprises:
    at least one member having a first portion including a first terminal endpoint and a second portion including a second terminal endpoint;
    at least one radiopaque connector joining the first terminal endpoint to the second terminal endpoint, wherein the at least one radiopaque connector is a separate element from the first and second terminal endpoints.

2. The stent of claim 1 wherein the at least one member comprises a first member and a second member, wherein each of the first member and second member comprises a first portion including a first terminal endpoint and a second portion including a second terminal endpoint, and wherein the at least one radiopaque connector comprises a first and second radiopaque connector, wherein each of the first and second radiopaque connectors joins a first terminal endpoint to a second terminal endpoint.

3. The stent of claim 1 wherein the at least one member comprises a plurality of members, each member having a first portion and a second portion, and wherein the at least one radiopaque connector comprises a plurality of radiopaque connectors, each of the plurality of radiopaque connectors joining the first terminal endpoint of the first portion of one of the plurality of members to the second terminal endpoint of the second portion of another of the plurality of members.

4. The stent of claim 1 wherein the at least one member comprises a wire or a filament.

5. The stent of claim 1 wherein the at least one member comprises a polymer.

6. The stent of claim 1 wherein the at least one member comprises a metal.

7. The stent of claim 1 wherein the at least one radiopaque connector comprises a polymer.

8. The stent of claim 7 wherein the polymer is selected from the group consisting of an adhesive polymer, a hot melt polymer, a silicone, and polyethylene terephthalate.

9. The stent of claim 1 further comprising at least one radiopaque marker at or near the second section of the tubular structure.

10. The stent of claim 9 wherein the at least one radiopaque marker at or near the second section of the tubular structure has a shape or pattern that is distinguishable from the at least one radiopaque connector when viewed by fluoroscopy.

11. A stent comprising:
    a tubular structure comprising:
        a first section comprising at least one radiopaque connector that joins a first terminal endpoint of a first portion of at least one member to a second terminal endpoint of a second portion of the at least one member, the at least one radiopaque connector forming a first radiopaque pattern, and
        a second section comprising at least one radiopaque marker forming a second radiopaque pattern that is different from the first radiopaque pattern when viewed under fluoroscopy, and
    wherein the tubular structure defines a lumen extending through the first section and the second section, and
    wherein the first section of the tubular structure is atraumatic.

12. The stent of claim 11, the tubular structure further comprising a medial section having a diameter smaller than at least one of the first section and the second section, the medial section extending between the first section and the second section.

13. The stent of claim 11 wherein tubular structure comprises a braid formed from the at least one member.

14. The stent of claim 11 wherein each of the radiopaque connectors is oriented generally parallel to the first portion or the second portion of the at least one member.

15. A method of manufacturing a stent comprising:
    forming a tubular structure having a first section and a second section, wherein the tubular structure defines a lumen extending through the first section and the second section,
    wherein the tubular structure comprises at least one member, each of the at least one member comprising a first portion having a first terminal endpoint and a second portion having a second terminal endpoint;
    joining at least one first terminal endpoint to a second terminal endpoint, wherein the joining comprises:
        contacting a radiopaque joining composition to the first terminal endpoint and the second terminal endpoint, wherein the radiopaque joining composition comprises a polymer and a radiopaque material;
    allowing the radiopaque joining composition to harden, thereby forming a radiopaque connector.

16. The method of claim 15 wherein joining at least one first terminal endpoint to a second terminal endpoint occurs at or near the first section of the tubular structure.

17. The method of claim 15 wherein forming a tubular structure comprises:
    braiding at least one member on a braiding mandrel.

18. The method of claim 17 wherein the joining occurs after the braiding.

19. The method of claim 15 further comprising:
    coating the tubular structure with a coating composition.

20. The method of claim 19, wherein the coating occurs after the joining.

* * * * *